United States Patent [19]

Dressel

[11] Patent Number: 4,985,027

[45] Date of Patent: Jan. 15, 1991

[54] SOFT TISSUE ASPIRATION DEVICE AND METHOD

[76] Inventor: Thomas D. Dressel, 8725 Walton Oaks CIr., Bloomington, Minn. 65438

[21] Appl. No.: 485,081

[22] Filed: Feb. 26, 1990

[51] Int. Cl.⁵ .............................................. A61B 17/36
[52] U.S. Cl. ...................................... 606/15; 128/395
[58] Field of Search .............................. 606/3, 13–16, 606/45, 46, 49; 128/395–398

[56] References Cited

U.S. PATENT DOCUMENTS

| | | | |
|---|---|---|---|
| 4,169,984 | 10/1979 | Parisi | 128/24 A |
| 4,515,583 | 5/1985 | Sorich | 604/22 |
| 4,531,934 | 7/1985 | Kossovsky et al. | 604/22 |
| 4,608,980 | 9/1986 | Aihara | 128/303.1 |
| 4,633,872 | 1/1987 | Chaffee et al. | 128/303.1 |
| 4,641,912 | 2/1987 | Goldenberg | 128/6 |
| 4,646,734 | 3/1987 | Cabrera et al. | 128/303.1 |
| 4,676,242 | 6/1987 | Doi | 128/303.1 |
| 4,735,605 | 4/1988 | Swartz | 604/22 |
| 4,775,365 | 10/1988 | Swartz | 604/119 |
| 4,784,649 | 11/1988 | Imonti et al. | 604/240 |
| 4,792,327 | 12/1988 | Swartz | 604/22 |
| 4,799,754 | 1/1989 | Goldenberg | 128/6 |
| 4,834,703 | 5/1989 | Dubrul et al. | 604/48 |
| 4,857,063 | 8/1989 | Glenn | 604/317 |
| 4,863,439 | 9/1989 | Sanderson | 604/264 |
| 4,886,491 | 12/1989 | Parisi et al. | 604/22 |

Primary Examiner—Max Hindenburg
Attorney, Agent, or Firm—Faegre & Benson

[57] ABSTRACT

A laser soft tissue aspiration device comprises an aspiration cannula housing a laser energy transmitting means for conducting laser energy to the site witin a patient's body for aspiration of soft tissue. The cannula is provided with an aspiration inlet port adjacent the cannula distal end. The proximal end of the cannula is provided with fluid flow connection to an aspiration source. A laser guide tube is additionally provided housing the laser energy transmitting means extending longitudinally within the cannula lumen from the laser energy source at the cannula proximal end and terminating at a point immediately prior to the aspiration inlet port. The tube also provides a conduit for transmitting cooling and cleaning fluid flow for the laser energy transmitting means.

A surgical method of aspirating soft tissue from a patient in vivo using this device is also provided transmitting means. Separated soft tissue and fluid is aspirated through the aspiration inlet port and the cannula by means of an aspiration source at the proximal end of the cannula.

13 Claims, 7 Drawing Sheets

SOFT TISSUE ASPIRATION DEVICE AND METHOD

FIELD OF THE INVENTION

This invention relates to a device and method for improving the surgical procedure of soft tissue removal by aspiration and more particularly to a device and method utilizing laser energy to more readily and safely facilitate the separating of soft tissue from a patient in vivo. This invention has immediate and direct application to the surgical procedure of liposuction or body contouring as well as application in the surgical procedures of other soft tissue removal such as brain tissue, eye tissue, and other soft tissue inaccessible to other soft tissue aspiration techniques.

BACKGROUND OF THE INVENTION

Within the past decade, the surgical use of lasers to cut, cauterize and ablate tissue has been developing rapidly. Advantages to the surgical use of laser energy lie in increased precision and maneuverability over conventional techniques. Additional benefits include prompt healing with less post-operative pain, bruising, and swelling. Lasers have become increasingly important, especially in the fields of Ophthalmology, Gynecology and Dermatology, as a less invasive, more effective surgical therapeutic modality which allows the reduction of the cost of procedures and patient recovery times due to diminished tissue trauma, bleeding, swelling and pain. The $CO_2$ laser has achieved wide spread use in surgery for cutting and vaporizing soft tissue. The $CO_2$ laser energy has a very short depth of penetration, however, and does not effectively cauterize small blood vessels. Other means such as electrocautery must be used to control and minimize blood loss. The Neodynium-YAG laser, on the other hand, because of its greater depth of tissue penetration, is very effective in vaporizing soft tissue and cauterizing small blood vessels. But as a result of this great depth of tissue penetration, the Neodynium-YAG laser has achieved limited use in the field of soft tissue surgery because of the possibility of unwanted damage to deeper tissues in the path of the laser energy beam.

Liposuction, a surgical technique of removing unwanted fat deposits for the purpose of body contouring, has achieved widespread use. In the United States, over 100,000 liposuction procedures were performed in 1989 alone. This technique utilizes a hollow tube or cannula with a blunt tip and a side hole or tissue aspiration inlet port near its distal end. The proximal end of the cannula has a handle and a tissue outlet port connected to a vacuum aspiration pump. In use, a small incision is made, the cannula tip and adjacent tissue inlet port is passed beneath the surface of the skin into the unwanted fat deposit. The vacuum pump is then activated drawing a small amount of tissue into the lumen of the cannula via the inlet port. Longitudinal motion of the cannula then removes the unwanted fat by a combination of sucking and ripping actions. This ripping action causes excessive trauma to the fatty tissues resulting in considerable blood loss and post-operative bruising, swelling and pain. Proposed advances in the techniques and apparatus in this field have been primarily directed to the design of the aspiration cannula, and more recently have involved the application of ultrasound and irrigation to melt and solubilize fatty tissue or the use of an auger, within the lumen of the cannula, to facilitate soft tissue removal. These proposed advances do not adequately address the goals of the surgical procedure: the efficient and precise removal of soft tissue with minimal tissue trauma and blood loss.

This invention utilizes a modification of a suction lipectomy cannula, already in clinical use, to position soft tissue within a protective chamber, allowing a Neodynium-YAG laser energy beam to cut and cauterize the soft tissue without fear of unwanted damage to surrounding or deeper tissues. This invention renders the removal of soft tissue safer, more precise, faster (and thus more efficient) and minimizes tissue trauma by eliminating the ripping action inherent in the conventional liposuction method.

This invention, by eliminating the ripping action of the conventional liposuction method, expands the scope of soft tissue removal. Currently, the liposuction method is limited to the aspiration of fat. Other soft tissues, such as breast tissue, lymphangiomas, and hemangiomas are too dense or too vascular to allow efficient and safe removal utilizing the liposuction method. This invention with the precise cutting and coagulating action of the Neodynium-YAG laser, within the cannula, permits the removal of these dense or vascular soft tissues.

This invention, by controlling the depth of penetration of the Neodynium-YAG laser within the protective aspiration cannula, expands the surgical applicability of the Neodynium-YAG laser. This laser can now be used, for example, in the precise removal of brain tissue without fear of unwanted damage to surrounding or deeper tissues. At this time, the $CO_2$ laser is extensively used for the vaporization of brain tumors, but because of its inability to effectively coagulate blood vessels, other methods such as electrocautery must be used to control blood loss during the procedure. In addition, because the vaporization of tissue generates large volumes of noxious and potentially toxic smoke, expensive, noisy and cumbersome suction devices must be used to eliminate the smoke from the surgical field. This invention, by utilizing the more effective coagulating power of the Neodynium-YAG laser, within the aspiration cannula, permits the combined action of tissue vaporization, control of blood loss, and elimination of smoke from the surgical field.

The basic design of the present Laser Soft Tissue Aspiration Device of this invention can be scaled down to permit soft tissue aspiration in other parts of the body. For example, an appropriately sized version of the present device can be used for safe removal of scar tissue from within the eye or adjacent to the retina and lens tissue from within the eye. Other appropriately sized and scaled versions of the present device may also be used for the removal of other unwanted soft tissues within the body. For example: removal of unwanted tracheal tissue, such as bronchial adenomas; removal of polyps and other soft tissue from within the lumen of the gastrointestinal tract; for endometrial ablations within the uterus; in conjunction with laparoscopic techniques to remove endometrial tissue with the abdomen.

BRIEF DESCRIPTION OF THE INVENTION

This invention provides a soft tissue aspiration device comprising an aspiration cannula and a fluid and laser fiber guide tube extending longitudinally within the cannula, the guide tube housing a laser energy transmitting fiber for conducting the laser energy to the soft tissue removal site within the patient's body and also housing a fluid flow path around the laser energy transmitting fiber. The aspiration cannula has a proximal and a distal end. The cannula is provided with a soft tissue aspiration inlet port adjacent to the cannula distal end. The proximal end of the cannula is attached to a handle which is provided with a fluid flow delivery port, a laser energy transmitting fiber inlet port, and an aspirated soft tissue outlet port. The fluid and laser fiber guide tube extends longitudinally from near the proximal end of the soft tissue aspiration device to a point immediately prior to the soft tissue aspiration inlet port within the cannula. A laser energy transmitting fiber extends from a laser energy source to the proximal end of the handle and longitudinally within the guide tube to a point immediately prior to the terminal point of the guide tube. Within the soft tissue aspiration device guide tube, the laser energy transmitting fiber is surrounded by fluid flow from a fluid source to the laser guide tube terminal point.

This invention also provides a surgical method of aspirating soft tissue from a patient in vivo using the device just described.

DETAILED DESCRIPTION OF THE INVENTION

Figure 1:
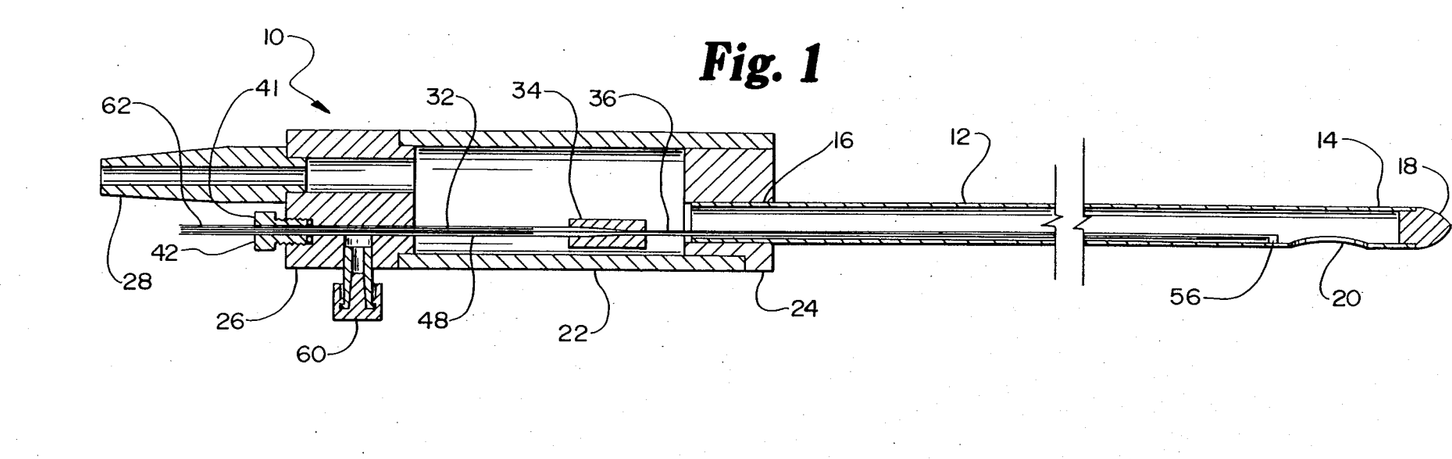
FIG. 1 is a side cut-away elevation view of a preferred soft tissue aspiration device of the present invention.
Figure 7:
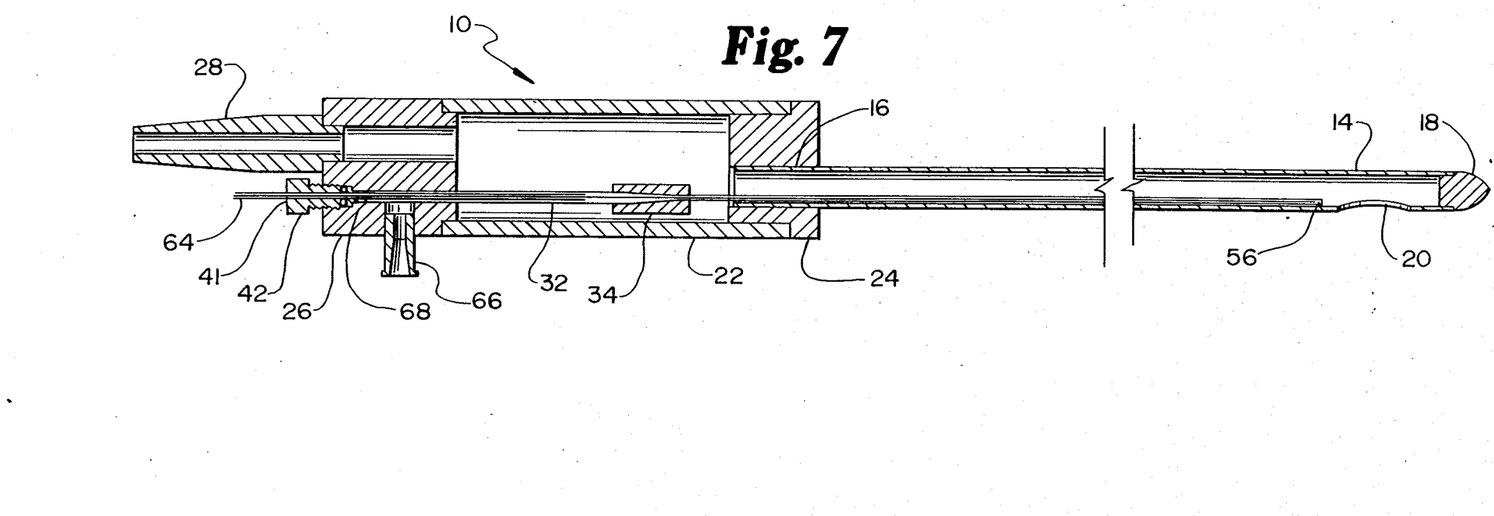
FIG. 7 is a side cut-away elevation view of the soft tissue aspiration device showing the optional fluid delivery port and bushing for use with alternative fiber optic delivery system.
Figure 10:
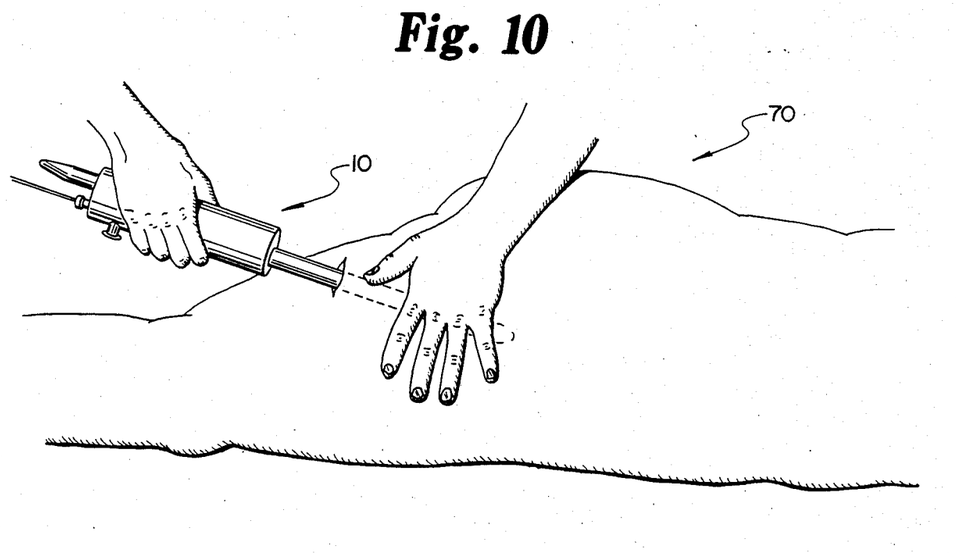
FIG. 10 is a cut-away detail of the laser soft tissue device of the present invention illustrated in position for performing liposuction within a fatty deposit of a body intermediate overlying epidermal layer and underlying muscle layer.

FIGS. 1, 7 and 10 illustrate a laser soft tissue device 10 according to the present invention. The device 10 includes an aspiration cannula 12 having soft tissue inlet port 20 adjacent to the distal end 14 and cannula tip 18.

Figure 2:
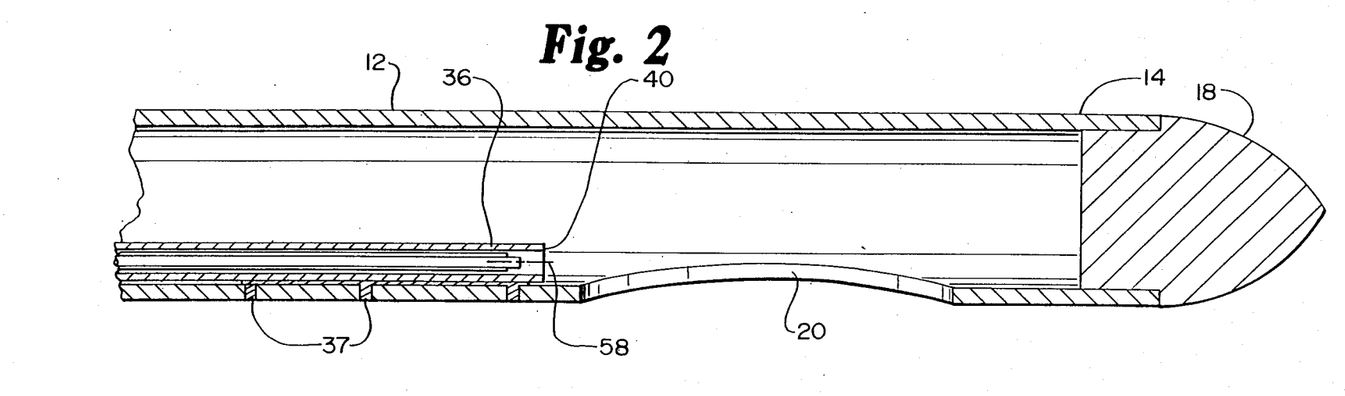
FIG. 2 is an exploded longitudinal section view of the distal end of the cannula.

As illustrated in FIGS. 1, 2 and 7, the cannula tip 18 can advantageously be a generally rounded, blunt or bullet shaped tip attached to the cannula 12 by welding or soldering. As illustrated in FIGS. 1 and 7, the cannula proximal end 16 is retained within the distal handle end cap 24, the aspirated soft tissue outlet port 28 is retained within the proximal handle end cap 26, and the distal handle end cap 24 and proximal handle end cap 26 are retained within the handle 22. The soft tissue outlet port is connected to an aspiration source by a plastic tubing (not shown).

Figure 3:
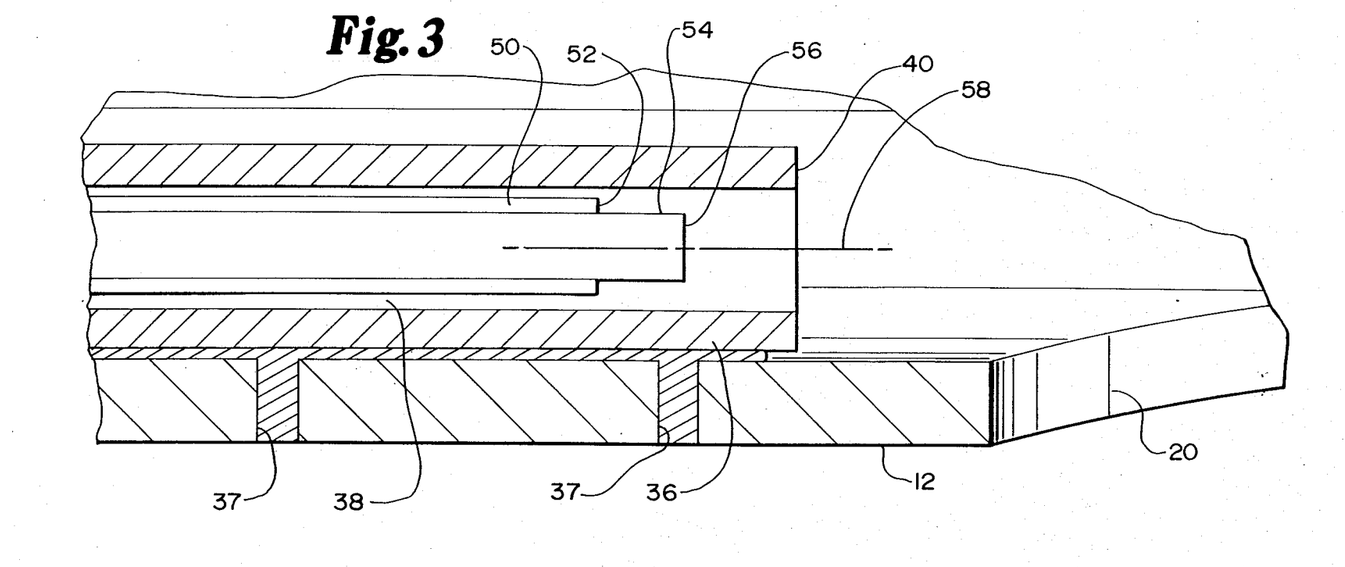
FIG. 3 is an exploded view similar to FIG. 2, showing the distal end of the laser fiber optic delivery system adjacent the soft tissue aspiration inlet port.
Figure 4:
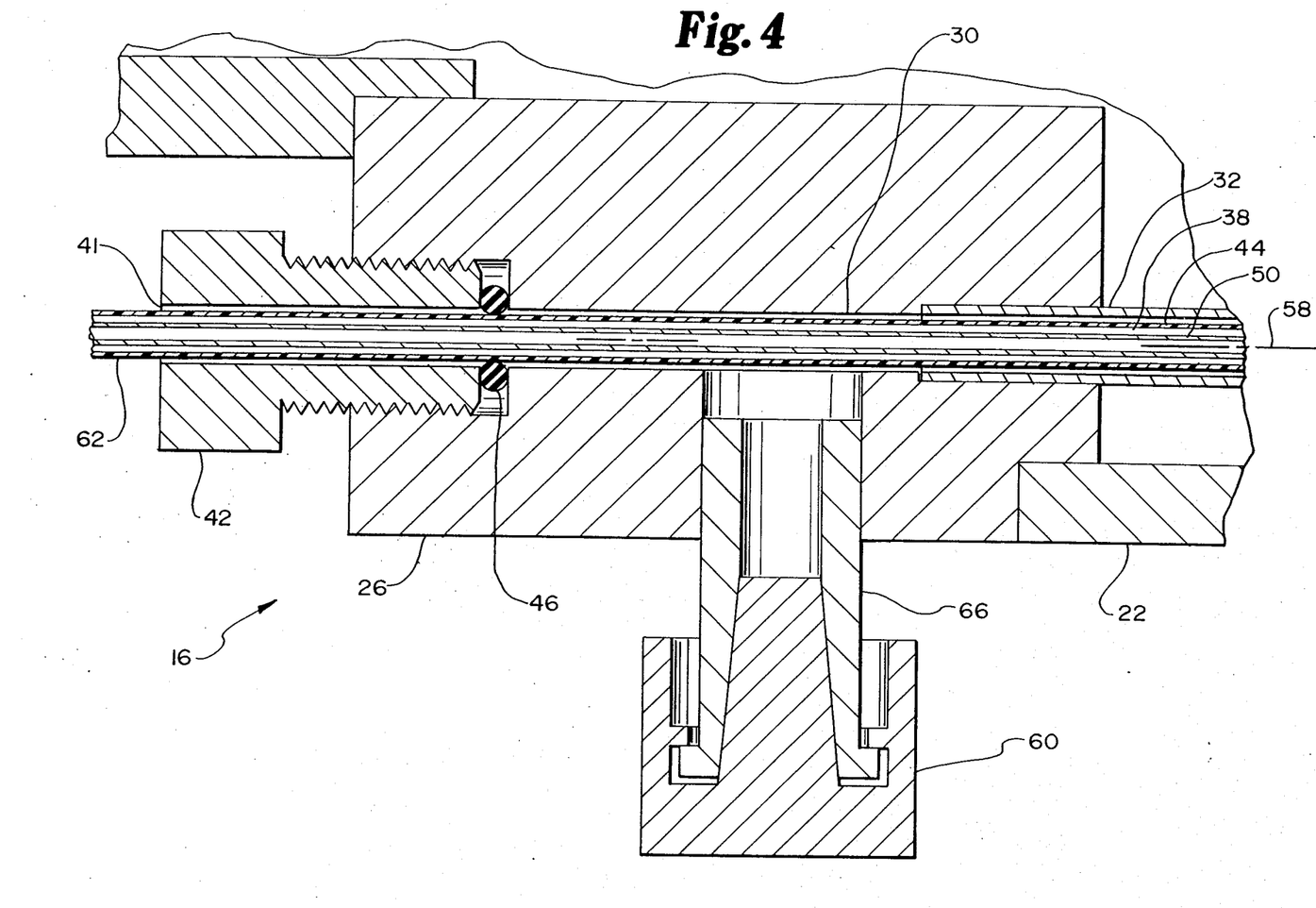
FIG. 4 is a partial exploded longitudinal section view of the handle and proximal end cap showing the attachments of the fluid and laser guide tube to the laser fiber and sources of fluid.
Figure 5:
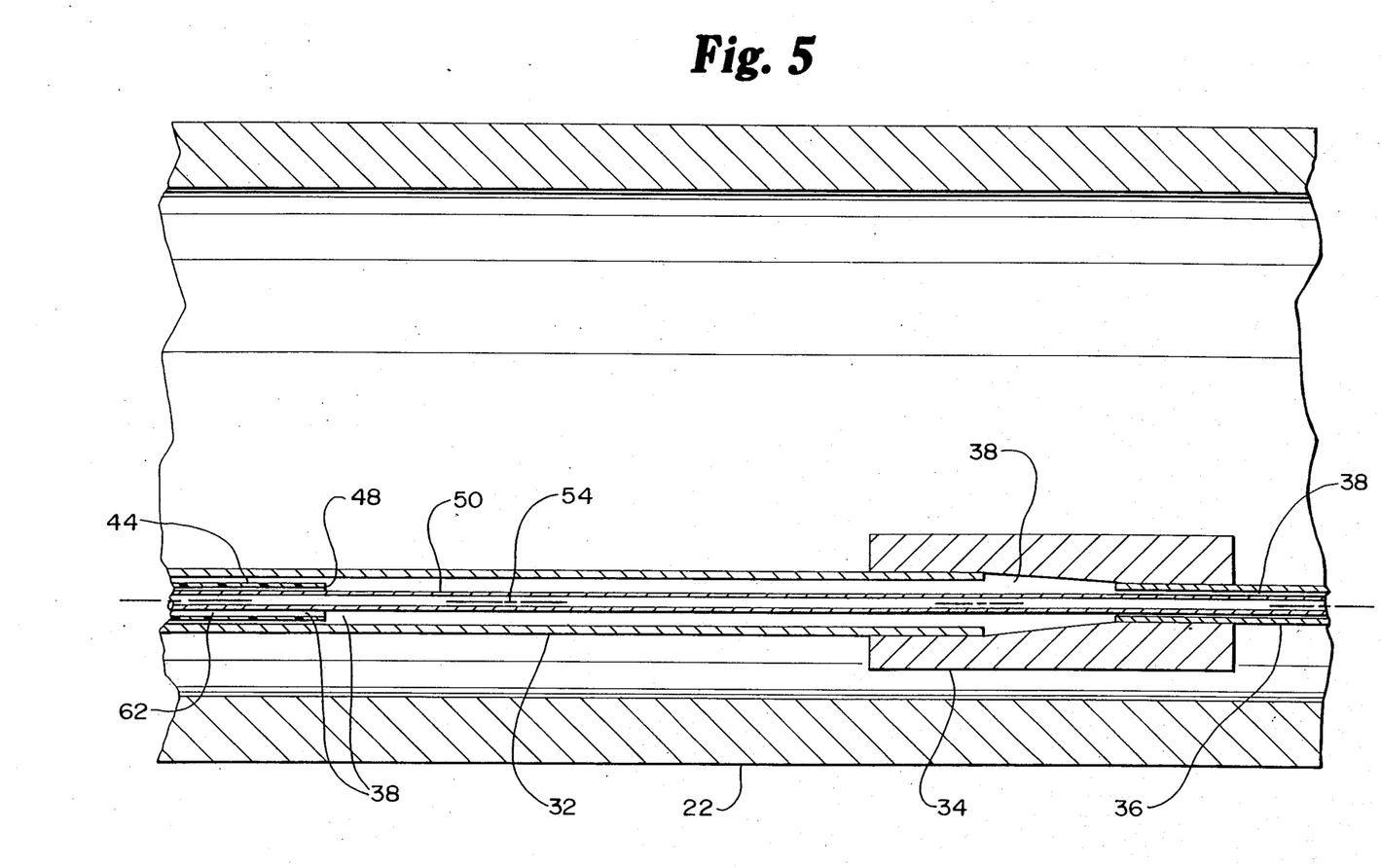
FIG. 5 is a partial exploded longitudinal section through the handle showing the fluid and laser fiber guide tube, Teflon coaxial fluid delivery tube and channel, and laser fiber.
Figure 6:
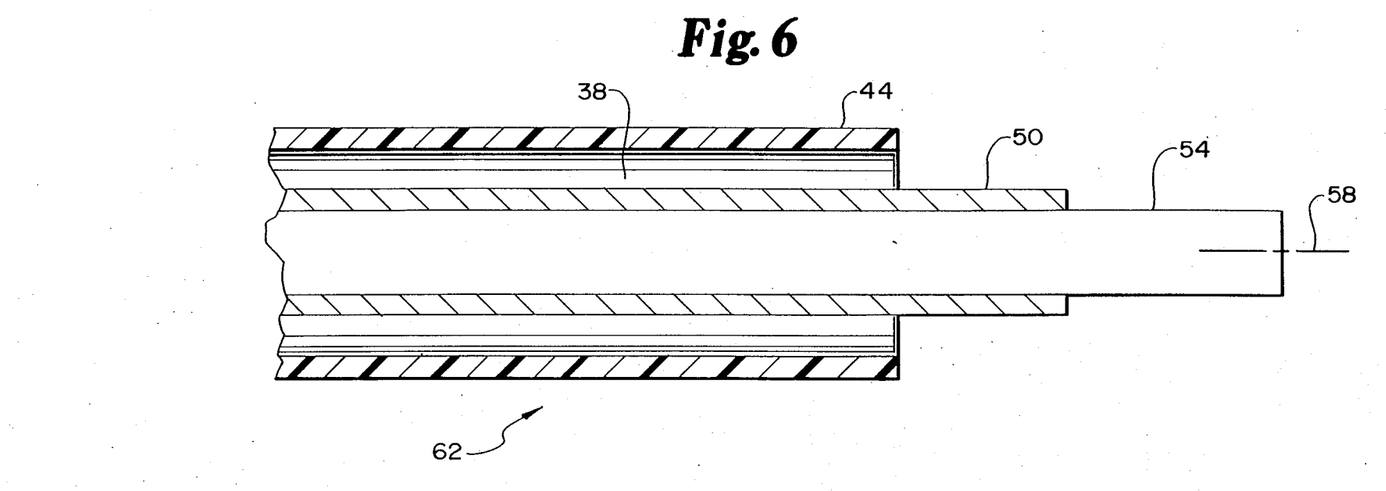
FIG. 6 is a partial exploded longitudinal section of the preferred laser fiber optic delivery system with Teflon coaxial fluid delivery tube.

As illustrated in FIGS. 1, 2, 3, 4, 5 and 7, a fluid and laser fiber guide tube extends longitudinally within the soft tissue aspiration device from the proximal handle end cap 26, at the laser energy source port 41, terminating at a point 40 immediately proximal to the soft tissue aspiration inlet port 20. The fluid and laser fiber guide tube consists of the coaxial fluid channel 30 drilled in the proximal handle end cap 26, the fluid and laser fiber large guide tube 32, the guide tube transition coupler 34, and the fluid and laser fiber small guide tube 36. The large guide tube 32 is of sufficient internal diameter (about 0.094") to accommodate the Teflon coaxial fluid delivery tube 44 (FIGS. 4, 5 and 6). The small guide tube is of sufficient internal diameter (about 0.054") to accommodate the Teflon laser fiber sheath 50 and laser fiber 54 and to provide clearance for the coaxial fluid channel 38 (FIGS. 3, 4 and 5). The guide tube transition coupler 34 is positioned within the handle 22 proximal to the proximal end of the cannula 16 and is drilled to accommodate the external diameters of the large 32 and small guide tubes 36. The guide tube components are joined together and to the proximal handle end cap 26 and within the aspiration cannula inner wall utilizing a means such as soldering or welding. The fluid and laser guide tube is provided with an O-ring seal 46 at its retention within the proximal handle end cap 26 at the laser energy source port 41.

Housed within the fluid and laser fiber guide tube is the laser fiber optic delivery system 62, shown in FIGS. 1, 2, 3, 4, 5 and 6, and consists of the Teflon coaxial fluid delivery tube 44, the Teflon laser fiber sheath 50, and the laser fiber 54, having laser discharge axis 58. The Teflon coaxial fluid delivery tube 44 is connected to a saline fluid source and pump integral with the laser energy source (not shown) and passes into the proximal end cap of the handle 16, through the fluid and laser guide channel 30 into the large guide tube 32, terminating at a point 48 within the large guide tube. The large guide tube 32 is maintained in position within cannula 12, for example, by silver solder through holes 37, as illustrated in FIGS. 2 and 3. The Teflon coaxial fluid delivery tube delivers cooling and irrigating fluid into the fluid and laser large guide tube 32, the fluid passes distally within the guide tube 32 surrounding the Teflon laser fiber sheath 50 and laser fiber 54 to the terminal point of the small guide tube 36. The laser fiber 54 constitutes the laser energy transmitting means, extending from the laser energy source (not Shown), through the energy source port 41 to a terminal point 56 immediately prior to the terminal point of the fluid and laser fiber guide tube 40. The retention of the laser fiber optic system 62 is accomplished by a retaining screw 42 at the fluid and laser energy source port 41.

Figure 8:
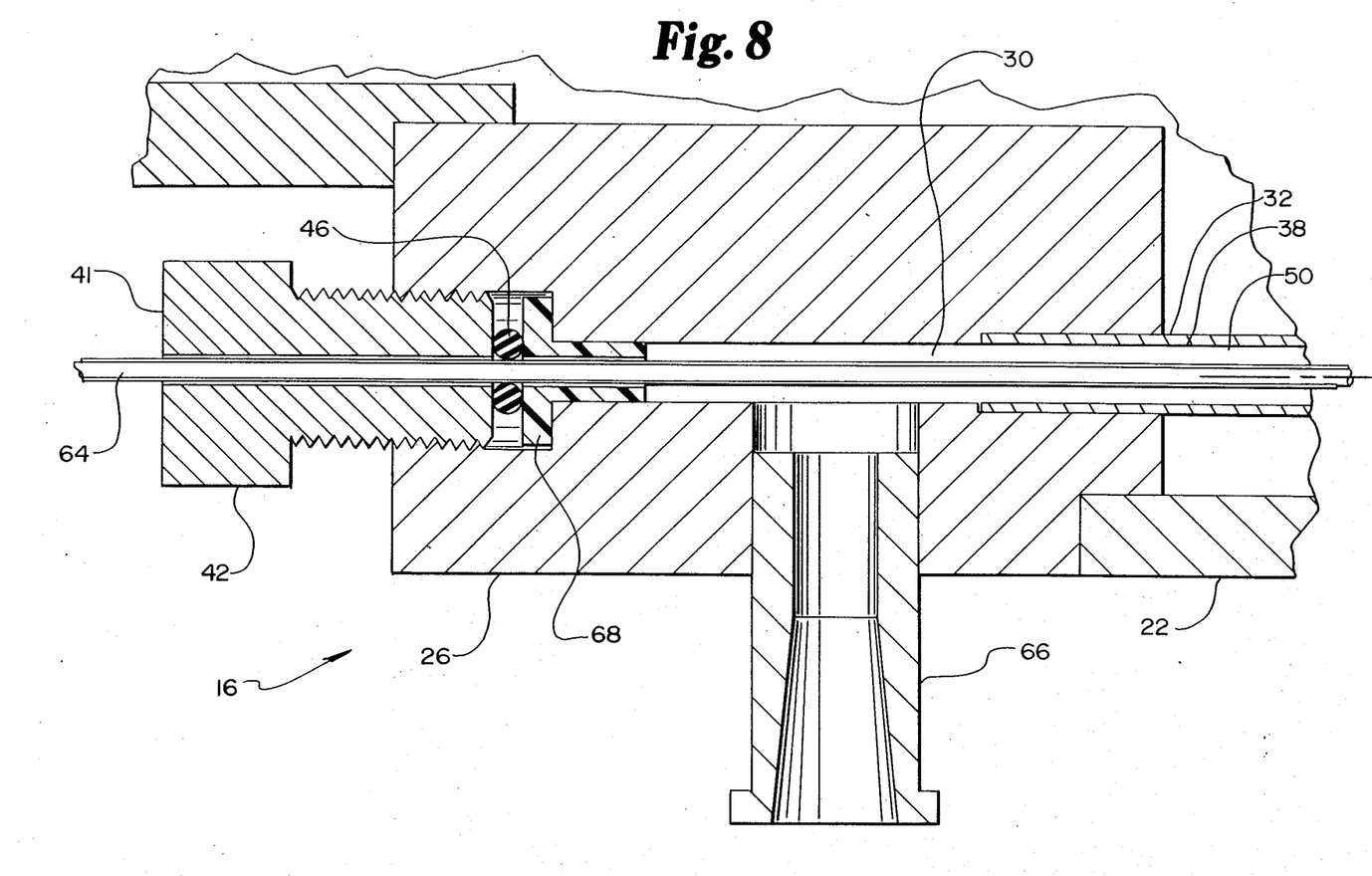
FIG. 8 is a partial exploded longitudinal section view of the handle and proximal end cap showing the attachments of the fluid and laser guide tube to the alternative fiber optic delivery system and source of fluid.
Figure 9:
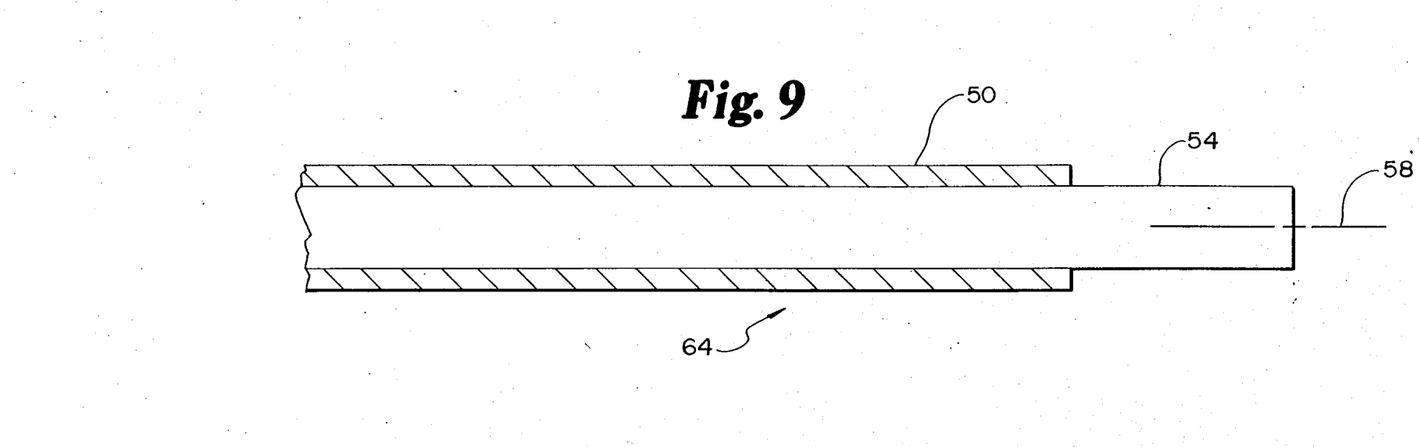
FIG. 9 is a partial exploded longitudinal section of the alternative laser fiber optic delivery system without Teflon coaxial fluid delivery tube.

FIGS. 7, 8 and 9 illustrate minor modifications of the preferred configuration of the present invention which allow the soft tissue aspiration cannula to accommodate an alternative fiber optic delivery system 64 (FIG. 9)

which does not incorporate a Teflon coaxial fluid delivery tube. A bushing 68 is positioned within the fluid and laser guide channel 30 to allow a fluid and air-tight seal at the fluid and energy source port 41. An optional fluid delivery port 66 is provided to allow the passage of cooling and irrigating fluid from a fluid source and pump (not shown). This port 66 is fitted with a fluid and air tight plug 60 when the Teflon coaxial fluid delivery tube is used.

As will be apparent to those skilled in this art, a shorter and thinner soft tissue aspiration cannula 12 will be useful in more restricted areas of the body, as under the chin, and a longer and larger diameter cannula will be useful in areas such as the thighs and buttocks where the cannula may be extended into soft tissue over a more extensive area. The length of the fluid and laser small guide tube 36 is determined by the length of the soft tissue aspiration cannula 12.

PREFERRED METHOD OF USE FOR LASER SOFT TISSUE ASPIRATION DEVICE

To perform the method of the present invention as illustrated in FIG. 10, the surgeon determines the location and extent of soft tissue to be removed. The appropriate size laser soft tissue aspiration device 10 is selected. A short incision is made and the cannula tip 18 and the distal end of the cannula 14 is passed into the soft tissue to be removed. The fluid delivery pump is activated, delivering normal saline through the Teflon fluid delivery tube 44, into the coaxial fluid channel 38, to the terminal point of the fluid and laser fiber guide tube 40. The application of a fluid flow of normal saline along the fiber to the fiber tip serves to cool the laser fiber 54 and maintain the terminal point of the laser fiber 56 and terminal point of the laser guide tube 40 free of tissue and other detritus. The aspiration pump is then activated. The negative pressure thus generated is transmitted to the laser soft tissue device 10 via a flexible suction tubing, to the soft tissue outlet port 28, through the handle 22, through the cannula 12, to the soft tissue aspiration inlet port 20. The resultant negative pressure thus generated is transmitted to the laser soft tissue device 10 via a flexible suction tubing, to the soft tissue outlet port 28, through the handle 22, through the cannula 12, to the soft tissue aspiration inlet port 20. The resultant negative pressure at the inlet port draws a small portion of the soft tissue into the lumen of the cannula 12, into the path of the laser discharge axis 58. The laser is then activated. The laser energy is transmitted to the terminal point of the laser fiber 56 and into the soft tissue within the cannula lumen, cleaving the soft tissue and coagulating small blood vessels. Additional soft tissue enters the soft tissue inlet port 20 by virtue of a reciprocating longitudinal motion of the laser soft tissue aspiration device 10 within the soft tissue. This reciprocating motion is applied by the surgeon's hand on the handle 22. The reciprocating motion of the laser soft tissue aspiration device, with respect to the surrounding soft tissue, is facilitated by the stabilization of the soft tissue by the surgeon's other hand placed on the skin overlying the cannula soft tissue inlet port 20. Soft tissue is removed from the vicinity of the inlet port 20 to the more proximal portion of the lumen of the cannula, and eventually out the cannula to the soft tissue outlet port 28 by the negative pressure generated by the aspiration pump.

The soft tissue aspiration cannula 12, cannula tip 18, handle 22, distal handle end cap 24, proximal handle end cap 26, aspirated soft tissue outlet port 28, fluid and laser fiber large guide tube 32, guide transition coupler 34, fluid and laser fiber small guide tube, and retaining screw 42 are all preferably of stainless steel. The soft tissue aspiration cannula 12 can be of appropriate sizes such as:

0.312" O.D.×0.016" wall (0.280" I.D.)
0.250" O.D.×0.016" wall (0.218" I.D.)
0.188" O.D.×0.016" wall (0.156" I.D.)
0.156" O.D.×0.016" wass (0.124" I.D.)

all of variable length. As will be apparent to those of skill in this art, a shorter and thinner diameter aspiration cannula will be useful in more restricted areas of the body, as around small appendages, and a longer and larger diameter cannula will be useful in areas, such as the thighs and buttocks, where the cannula may be extended into fatty tissue over a more extensive area. The cannula tip 18 is in sizes of the same diameter as the aspiration cannula O.D., machined to a blunt tip and to fit the cannula inside diameter. The handle 22 is preferably of tubing of 1.125" O.D.×0.125" wall (1.0" I.D.) about 3.25" long. The distal handle end cap 24 is preferably of 1.125" diameter, machined to fit the handle inside diameter and drilled to accommodate the aspiration cannula outside diameter. The proximal handle end cap 26 is preferably of 1.125" diameter, machined to fit the handle inside diameter, drilled to accommodate the aspiration outlet port, fluid and laser guide channel, and large guide tube, and drilled and tapped to accommodate the retaining screw. The aspirated soft tissue outlet port 28 is perferably of 0.75" diameter, machined to fit the proximal handle end cap and tapered to accommodate ⅜" I.D.×½" O.D. suction tubing, and drilled to a 0.3125" diameter hole. The fluid and laser fiber large guide tube 32 is preferably 0.120" O.D.×0.013" wall (0.094" I.D.), about 2 " long. The guide tube transition coupler 34 is preferably 0.25" diameter 0.625" long, drilled to accommodate large and small guide tubes 32 and 36. The fluid and laser fiber small guide tube 36 is preferably of 0.072" O.D.×0.009" wall (0.054" I.D.) in variable lengths, determined by the length of the cannula 12. Retaining screw 42 is preferably ¼"-28 threads/inch Allen head cap screw 0.75" long, drilled to accommodate the laser fiber optic delivery system. Plug 60 for fluid source port 66 is preferably a Luer-Lock male plug. The preferred laser fiber optic delivery system 29 is available from, for example, Surgical Laser Technologies, Malvern, Penna., Model number: SFE 2.2

2.2 mm (0.086") O.D. Teflon coaxial fluid delivery tube
0.8 mm (0.315") O.D. Teflon laser fiber sheath
0 600 mm (0.023") diameter laser guide fiber fiber length 4.0 meters (157.5")

The alternative laser fiber optic delivery system is available from, for example, Heraeus LaserSonics, Inc., Santa Clara, Calif., model number: B24D 0.8 mm (0.315") O.D. Teflon laser fiber sheath
0.600 mm (0.023") diameter laser guide fiber fiber length 3.66 meters (144")

Fluid delivery port 66 is preferably a stainless steel female Luer-Lock. Bushing 68 for laser fiber sheath 50 is preferably of Teflon 0.120" O.D.×0.072" I.D., 0.187" diameter flange, 0.5" long, approximate dimension.

A preferred laser source for use with preferred device 10 of this invention is available, for example, from Surgical Laser Technologies, Malvern, Penna., model number SLT CL60, power delivery 0 to 40 watts, with a fluid delivery pump. An alternative laser source for use with alternative device 70 of this invention is available, for example from Cooper LaserConics, Inc. Santa Clara, Calif., model number: 800, power delivery 0 to 100 watts. The suction tubing is available, for example, from Dean Medical Instruments, Inc. Carson, Calif., preferably $\frac{3}{8}''$ I.D.$\times \frac{5}{8}''$ O.D. The vacuum aspirator can be of any suitably type, such as that available from WElls Johnson Co., Tucson, Ariz., model: General Aspirator, vacuum 0 to 29+ CFM. The fluid pump for delivering the cooling and cleaning lavage can be of any suitably type, such as that available from Imed Volumetric Infusion pump, Model No. 960, available from Imed Corporation, San Diego, Calif.

By utilizing the present laser soft tissue aspiration device according to the present method, a variety of advantages are achieved. The ND:YAG laser energy will decrease blood loss and render the surgical procedure safer by coagulating small blood vessels in the surgical area. By enabling the cutting of the soft tissue in a straighter line, the scooping, ripping and tearing action characteristic of other devices, will be eliminated, resulting in fewer contour irregularities and enhanced satisfaction. With the addition of the cutting action of the laser energy provided by the present invention the rate of removal of unwanted soft tissue is greatly enhanced over that of previous devices and techniques thus decreasing operative time. By completely confining the laser energy safely and efficiently within the lumen of the cannula, these benefits are obtained without fear of peripheral laser thermal damage. The fluid flow, in addition to providing cooling and cleaning of the laser fiber, will prevent tissue adherence to and potential damage to the sensitive laser fiber tip. The fluid flow will also assist in solubilizing and emulsifying the fatty tissue serving to further facilitate aspiration and prevent clogging of the cannula throughout the procedure.

Thus, the present invention provides an improved device for use in surgical removal of soft tissue. Animal studies and clinical procedures to date utilizing the present invention for surgical body contouring by removing fat have demonstrated less bleeding, less post-operative pain and bruising, excellent cosmetic results, and generally a more aesthetic procedure than has been possible with previous soft tissue aspiration techniques.

That which is claimed is:

1. An in vivo surgical method of aspirating soft tissue from a patient comprising:
    inserting an aspiration cannula through the patient's epidermis, so that a distal end of the cannula is positioned in an area of soft tissue, said cannula provided with a central lumen in communication with an aspiration inlet port adjacent the cannula distal end;
    providing laser energy from a laser energy source to a laser energy transmitting means operatively mounted in a laser guide tube, said guide tube mounted for longitudinally extending within the cannula lumen, for transmitting laser energy to a point adjacent said aspiration inlet port to perform localized soft tissue cutting and blood vessel coagulation;
    transmitting fluid through said guide tube in flow contact with said laser transmitting means to provide cooling for and cleaning of said laser transmitting means; and
    providing a source of aspiration at a proximal end of said cannula to aspirate soft tissue through said aspiration inlet port and said cannula.

2. The method of claim 1, wherein the soft tissue is fatty tissue between the patient's epidermis and muscle.

3. The method of claim 1, wherein the soft tissue is located within the brain, the eye, the trachea or the abdomen.

4. The method of claim 1, wherein the cannula distal end is generally rounded or bullet-shaped to facilitate insertion into the patient's tissue with a minimum of localized tissue trauma.

5. The method of claim 1, wherein the laser energy source if a neodynium-YAG laser which functions to cut soft tissue and coagulate small blood vessels.

6. The method of claim 1, wherein the laser energy transmitting means is completely contained within the cannula lumen and is constructed and arranged so that only tissue within the cannula is exposed to operative amounts of laser energy.

7. The method of claim 1, wherein the fluid flow provides cooling and cleaning of the laser energy transmitting means and prevents tissue adherence to and damage of the laser energy transmitting means distal end.

8. A laser soft tissue aspiration device comprising:
    an aspiration cannula having a proximal and a distal end, the cannula provided with an aspiration inlet port adjacent the cannula distal end and having a lumen provided with fluid flow connection to an aspiration source at the cannula proximal end;
    a laser guide tube extending longitudinally within the cannula lumen, said laser guide tube extending from a laser energy source at the cannula proximal end and terminating at a point immediately adjacent to the aspiration inlet port; and
    laser energy transmitting means within said tube, said laser energy transmitting means extending from a laser energy source at the cannula proximal end to a point immediately prior to the laser guide tube termination point;
    said tube also providing a conduit for transmitting fluid flow from a fluid flow source at the cannula proximal end in intimate contact with said laser energy transmitting means to the laser guide tube termination point.

9. A laser liposuction device according to claim 8, wherein the laser energy source is a neodynium-YAG laser.

10. A laser liposuction device according to claim 8, wherein the aspiration cannula is formed of stainless steel and is formed with a generally rounded or bullet-shaped distal end.

11. A laser liposuction device according to claim 8, wherein the length of the cannula is between about 11 inches to about 18 inches in length, and the outside diameter is between about 0.156 inches to about 0.312 inches.

12. A laser liposuction device according to claim 8, wherein the proximal end of the laser guide tube is provided with an O-ring seal.

13. A laser liposuction device according to claim 8, wherein the laser energy transmitting means is a fiber optic delivery system.

* * * * *